(12) United States Patent
Blanco Guillermo et al.

(10) Patent No.: US 8,251,927 B2
(45) Date of Patent: Aug. 28, 2012

(54) SYSTEM AND PROCEDURE FOR THE ANALYSIS OF THE SWALLOWING PROCESS IN HUMANS

(75) Inventors: Alfonso Blanco Guillermo, Barcelona (ES); Pere Clave Civit, Barcelona (ES)

(73) Assignee: Image & Physiology, S.L., Barcelona (ES)

( * ) Notice: Subject to any disclaimer, the term of this patent is extended or adjusted under 35 U.S.C. 154(b) by 643 days.

(21) Appl. No.: 11/596,667

(22) PCT Filed: Apr. 20, 2005

(86) PCT No.: PCT/EP2005/004252
§ 371 (c)(1),
(2), (4) Date: Nov. 16, 2006

(87) PCT Pub. No.: WO2005/111904
PCT Pub. Date: Nov. 24, 2005

(65) Prior Publication Data
US 2008/0064990 A1 Mar. 13, 2008

(30) Foreign Application Priority Data
May 17, 2004 (ES) .................................. 200401179

(51) Int. Cl.
*A61B 5/103* (2006.01)
(52) U.S. Cl. ...................................................... 600/590
(58) Field of Classification Search .................... 600/407
See application file for complete search history.

(56) References Cited

U.S. PATENT DOCUMENTS

| | | | | |
|---|---|---|---|---|
| 5,090,042 | A * | 2/1992 | Bejjani et al. | 378/98.2 |
| 5,143,087 | A * | 9/1992 | Yarkony | 600/593 |
| 6,511,426 | B1 * | 1/2003 | Hossack et al. | 600/437 |
| 2005/0065450 | A1 * | 3/2005 | Stuebe et al. | 600/547 |
| 2005/0124888 | A1 * | 6/2005 | Jjt Rein et al. | 600/443 |
| 2005/0283064 | A1 * | 12/2005 | Gross et al. | 600/407 |

OTHER PUBLICATIONS

Dengel et al. "Image processing in swallowing and speech research".*
Dengel et al, *Dysphagia*, 6(1):30-39 (1991).
Perlman et al, *Dysphagia*, 17(2):162-167 (2002).

(Continued)

*Primary Examiner* — Tse Chen
*Assistant Examiner* — Hien Nguyen
(74) *Attorney, Agent, or Firm* — Sughrue Mion, PLLC

(57) ABSTRACT

Computer-implemented system (1) for the analysis of the swallowing process in humans, which comprises an exposure unit (2) of the individual's head and neck area to external stimuli (3); a data capture unit (4) of data from the response to external stimuli; a data digitization unit (5); a digitized data processing unit (6); a memory unit (7); a processed data display unit (8), with the digitization unit (5), the memory unit (7) and the data display unit (8) being controlled by a computer program, wherein the external stimuli (3) consist of electromagnetic radiation; and where the data from the response to the external stimuli (3) consist of a continuous data sequence, which can be temporally and/or spatially analyzed and parametrized. The invention also relates to a computer-implemented procedure for the analysis and quantification of the swallowing process in humans.

19 Claims, 4 Drawing Sheets

OTHER PUBLICATIONS

Potratz J.R. et al; "A comparison of swallowing in three subjects using an interactive image processing system", Proceedings of the Annual Symposium on Computer Based Medical Systems. Durham, Jun. 14-17, 1992; [Proceedings of the Annual Symposium on Computer Based Medical Systems], pp. 115-122, XP010028196r.

Clave P., Terre R, de Kraa M., Serra M. Approaching oropharyngeal dysphagia. Rev Esp Enferm Dig. Feb. 2004, 96(2):119-31. Review. English, Spanish. PubMed PMID: 15255021.

Clave P., Terre R, de Kraa M., Girvent M., Palomera E., Bernabeu M., Serra-Prat M., Characterization of Oropharyngeal Swallow Motor Pattern in Patients with Neurogenic Dysphagia; Digestive Disease Week Conference; New Orleans; presented May 18, 2004.

* cited by examiner

SYSTEM AND PROCEDURE FOR THE ANALYSIS OF THE SWALLOWING PROCESS IN HUMANS

CROSS-REFERENCE TO RELATED APPLICATION

This application is a 371 of PCT/EP2005/004252, filed Apr. 20, 2005; the disclosure of which is incorporated herein by reference.

TECHNICAL FIELD OF THE INVENTION

The present invention relates to a system for the analysis of the swallowing process in humans, which comprises a unit to expose the head and neck area of the individual to external stimuli; a data capture unit of data from the response to external stimuli; a data digitization unit; a digitized data processing unit; a memory unit; a processed data display unit, with the digitization unit, the memory unit and the data display unit being controlled by a computer program. The invention also relates to a procedure for the analysis of the swallowing process, which consists of exposing the area between the head profile and the neck of the individual to electromagnetic radiation whilst a radiographic contrast substance is swallowed.

BACKGROUND OF THE INVENTION

Analysis of the swallowing process in humans has been performed for the last couple of decades, with the purpose of detecting abnormalities which may be the cause of notable pathologies and infections, e.g. if inhalation occurs during the swallowing process, there is the risk of material entering inside the respiratory tract and it may cause pulmonary infections. In the same way, disturbances may occur in the efficiency of transporting the bolus, which may lead to malnutrition. Abnormal swallowing receives the name dysphagia.

The swallowing process is generally studied by exposing a patient to x-rays whilst he/she is made to swallow a radiographic contrast substance. Simultaneously, the process is recorded by a video camera so that the doctor can analyse the movement of said oropharyngeal structures involved in said process. This type of diagnostic procedure is called a videofluoroscopic swallow study or MBS (modified barium swallow).

Specifically, it has been determined that the forwards and upwards movement of the hyoid bone and the upwards movement of the larynx, are two important elements in the cricopharyngeal region opening process and in the laryngeal vestibule closure process.

The problem with the means currently used to analyse the swallowing process is that they do not permit a real-time diagnosis to be obtained, due to the fact that, for a verdict to be given, the doctor should view the same swallowing event several times to determine at what point in the section or path of the material or liquid the anomaly or dysphagia occurs. Furthermore, said study is currently qualitative, which in many occasions makes it difficult to determine the degree or level of dysfunction. Since all the events of the swallowing act occur in under a second, many of the dysfunctions of patients with dysphagia are revealed in time intervals which cannot be seen by the human eye when they are observed at the rate at which they normally occur.

In an attempt to quantify the swallowing process, in "Interactive Computer Program for Biomechanical Analysis of Videoradiographic Studies of Swallowing" (AJR 153:277-280, 1989), Logemann et al. disclose a computer program to digitize frozen images and represent the position of anatomic structures in the oral and pharyngeal cavities therein. To do this, they digitize frozen images recorded on video; they identify several anatomical reference points in each image; they then identify anatomical points of interest; and via the computer program or software medium, they calculate the spatial coordinates of said anatomical points of interest in each one of the previously digitized images. This software provides quantitative information on the position of the structures which can then be processed to produce time-dependent arrangement graphics of said structures. The doctor first selects the individual images which he/she wants to digitize, next, the programs analyse them in the order pre-established by the user. In any case, quantitative analysis using this method takes a long time, information is lost, as the method only permits the analysis of spatial and not temporal events; and the image-to-image analysis does not allow the process to be viewed in real time.

From the state of the art, we can deduce the need for a system to study and analyse the swallowing process which permits making a real-time analysis with greater precision. The present invention provides numerous advantages with respect to the procedures and equipment or systems for the analysis of swallowing in humans, while resolving the previously posed problems.

EXPLANATION OF THE INVENTION

The computer-implemented system for the analysis of the swallowing process in humans object of the invention, which comprises a unit to expose the individual's head and neck area to external stimuli, characterized in that the data from the response to the external stimuli consist of a continuous data sequence which, by means of the action of a processing unit, can be qualitatively or quantitatively analysed and parametrized with regard to temporal and/or spatial reference systems; and, in that the display unit consists of a display and processing unit which displays said continuous data sequence at a rate equal to the actual rate of the swallowing process or at a rate resulting from multiplying the actual rate by a coefficient which is selectable by the user.

According to another characteristic of the invention, the coefficient selectable by the user is preferably less than one.

The computer-implemented system is also characterized in that the external stimuli consist of electromagnetic radiation.

According to another characteristic of the computer-implemented system according to the invention, the electromagnetic radiation consists of x-rays and the continuous data sequence from the response to external stimuli are x-ray contrast images.

The system is also characterized in that the data capture unit comprises a video camera.

Another object of the invention is a computer-implemented procedure for the analysis of the swallowing process or the oropharyngeal motor response in humans, characterized in that comprises the stages of:

a) capture and adaptation of data from the capture unit in a continuous data sequence;

b) digitization of the continuous data sequence from the data capture unit;

c) processing of the digitized data and storing them in the memory, so that the digitized data sequence can then be displayed at the actual rate of the swallowing process or at a rate which is the result of multiplying the actual rate by a coefficient selectable by the user;

d) determination of a spatial axis (x-y-z) and an initial reference instant (T=0) in the data sequence, e) display or viewing of the data sequence at the actual rate of the swallowing process or at a rate which is the result of multiplying the actual rate by a coefficient selectable by the user;

f) parametrization with respect to the initial reference instant (T=0) of one or several events or points in the swallowing process time, said swallowing process being represented by the continuous data sequence;

g) parametrization with respect to a spatial reference axis (x-y-z) of one or several spatial points corresponding to arrangements of anatomic structures involved in the swallowing process represented by the continuous data sequence;

h) comparison of the interval of the parametrized points with standardized templates; and i) representation of the temporal events and/or of the parametrized spatial arrangements.

j) Storage of the continuous sequences of data parametrized in the memory unit.

According to another characteristic of the invention, the procedure for the analysis of the swallowing process is characterized in that the data are images and the continuous data sequence is a film.

The procedure for the analysis of the swallowing process is also characterized in that the parametrization of one or several events or points in the swallowing process time, consists of the parametrization of at least one of the following events: the moment of opening and/or closure of the glossopalatine seal; the moment of opening and/or closure of the velopharyngeal seal; the moment of opening and/or closure of the laryngeal vestibule; and the moment of opening and/or closure of the upper oesophageal sphincter.

According to another characteristic of the procedure object of the invention, the parametrization of one or several spatial points corresponding to the arrangement of anatomic structures, involved in the swallowing process represented by the continuous data sequence, consists of the parametrization of at least one of the following arrangements of anatomical structures: the arrangement of the hyoid bone, the arrangement of the arytenoids cartilage, and the arrangement of the front or rear edge of the upper oesophageal sphincter.

The procedure object of the invention is also characterized in that the electromagnetic radiation consists of x-rays.

BRIEF DESCRIPTION OF THE DRAWINGS

The attached drawings illustrate, by way of non-limiting example, an embodiment of the computer-implemented system and procedure for the analysis of the swallowing process in humans according to the invention. In said drawings.

DETAILED DESCRIPTION OF THE DRAWINGS

The system for the analysis of the swallowing process in humans of the present invention comprises different units coordinated to perform the stages of the procedure.

Figure 1:
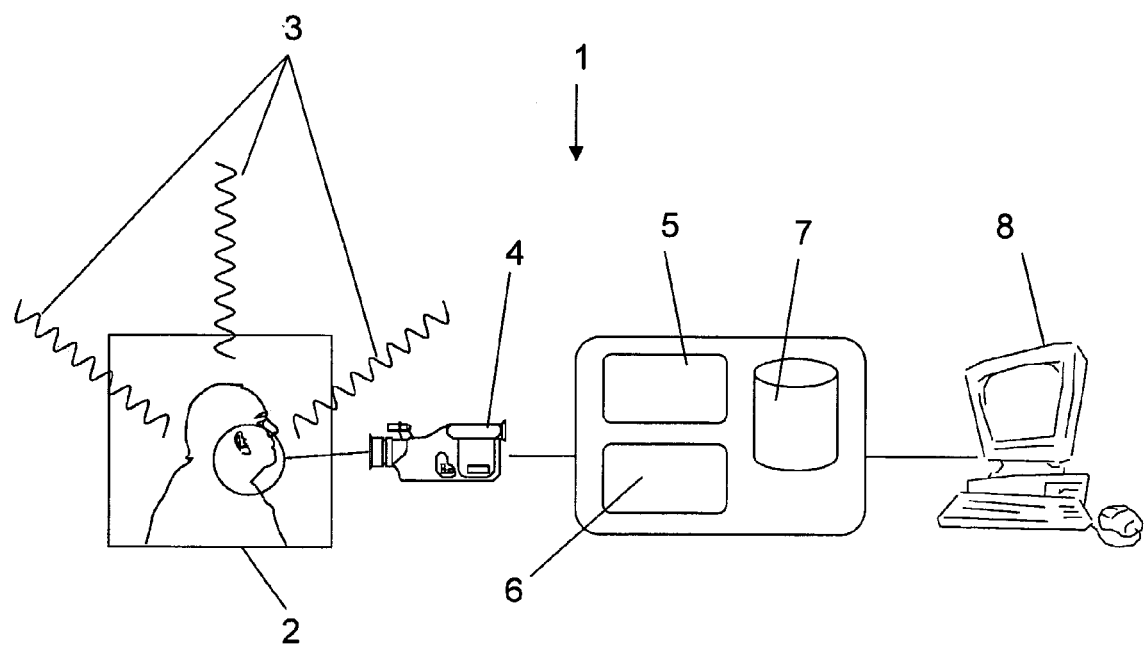
FIG. 1 is a diagram of the system for the analysis of the swallowing process in humans according to the invention.

The units which comprise the system are diagrammatically represented in FIG. 1. The system 1 comprises a unit 2 to expose of the individual's head and neck area to external stimuli 3; a data capture unit 4 of data from the response to external stimuli; a data digitization unit 5; a digitized data processing unit 6; a memory unit 7 and a processed data display unit 8.

The external stimuli 3 consist of electromagnetic radiation. Specifically, the electromagnetic radiation corresponds to x-rays, although any type of radiation is also applicable with the objective of capturing data or images of the exposed area.

The data capture unit 4 in accordance with FIG. 1 corresponds to a camera, which may be analog or digital, and which records images from the exposure unit 2 of the individual to electromagnetic radiation. Evidently, said capture unit 4 can be represented by any type of camera or image recording apparatus. Said images or data from the response to the external stimuli, are digitized in a unit 5 connected to the data capture unit 4, which transforms them in a continuous data sequence or digital images, so that information from the swallowing process is not lost. Once digitized, the continuous data sequence is processed in the processing unit 6, which means it can be displayed at a rate equal to the actual rate of the swallowing process or at a rate which is the result of multiplying the actual rate by a coefficient selectable by the user. Generally, said coefficient is less than one. Using the memory unit 7, all the data is stored at all times.

The display unit 8, which in the case represented corresponds to a computer screen, allows the continuous data sequence to be displayed and the external processing thereof by display at the actual rate of the swallowing process or at a rate which is the result of multiplying the actual rate by a coefficient selectable by the user which, as previously mentioned, is preferably less than one.

Figure 2:
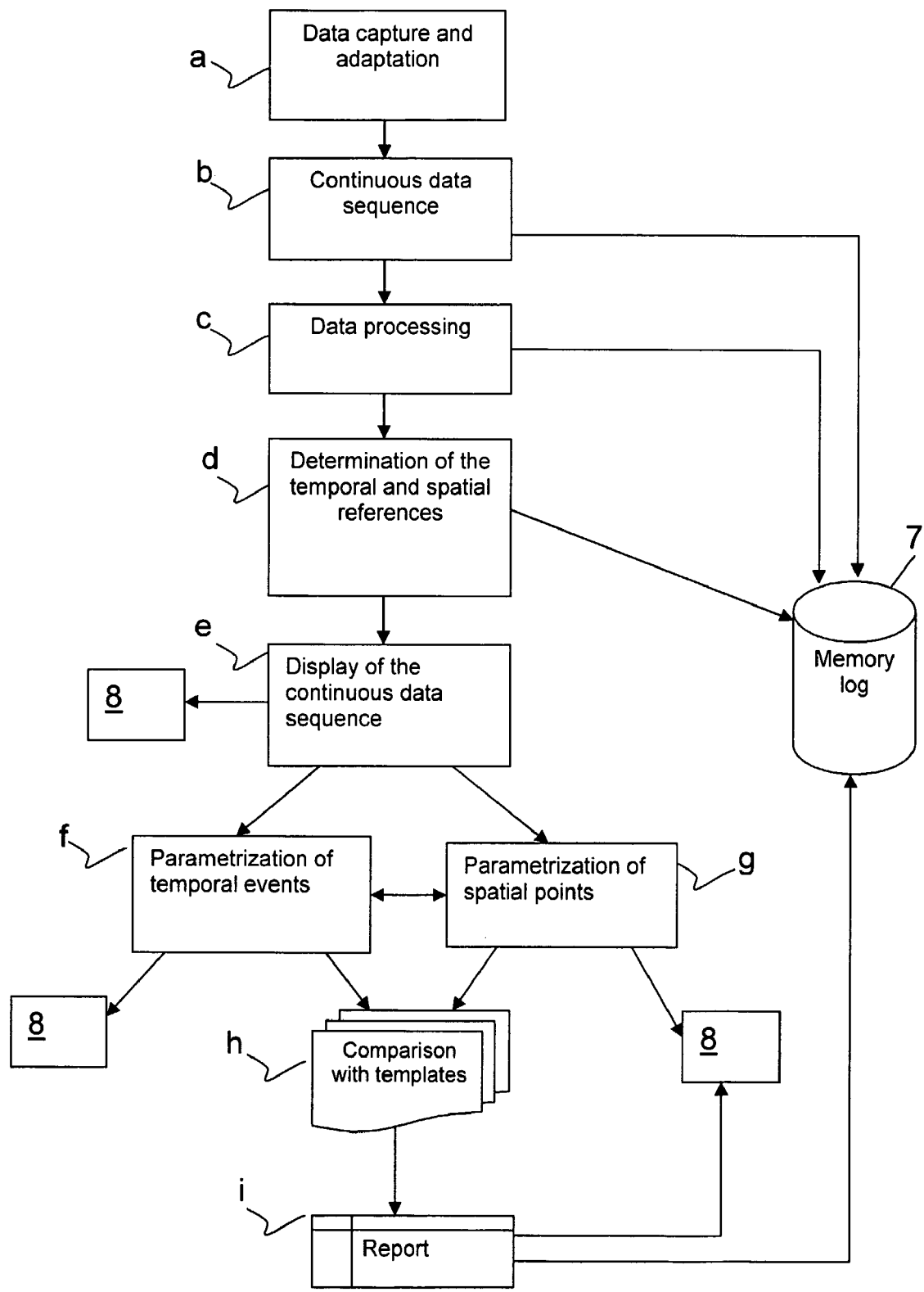
FIG. 2 is a block diagram summarising the working procedure for the analysis of the swallowing process in humans according to the invention.

FIG. 2 represents in block diagrams, a scheme with the stages of the procedure followed by the system for the analysis of the swallowing process or of the oropharyngeal motor response.

In a first stage a), the data from the response to the electromagnetic radiation or other external stimuli 3, after the individual's neck and head area is exposed to them while he/she swallows the substance, are captured and adapted to form a continuous data sequence. Next, in a second stage b) the continuous data sequence is digitized and processed in stage c) so that said sequence can then be displayed at the actual rate of the swallowing process or at a rate which is the result of multiplying the actual rate by a coefficient selectable by the user. By combining stages b) and c) of the procedure, the continuous data sequence or images can be displayed at a rate slower that that typical of the swallowing process.

Once the continuous data sequence is digitized and processed it can be displayed by the display and processing unit 8, and in stage d), using viewed or displayed data, it determines a spatial axis (x-y-z) and an initial reference instant (T=0) in the data sequence.

Next, once the reference systems are established, in two subsequent stages f) and g), one or several time events and/or one or several spatial points corresponding to specific anatomical structures, are parametrized and compared with standardized templates h).

The analysis procedure provides that the spatial points or temporal events of the continuous data sequence that have been parametrized can be represented in graphics 14 at a later stage i). Said graphics or tables 14 are saved in the memory unit 7 and can be displayed at all times on the display unit 8 or on paper records (Report). All of this in a form typical of the representation of data using computer-implemented systems.

Figure 3:
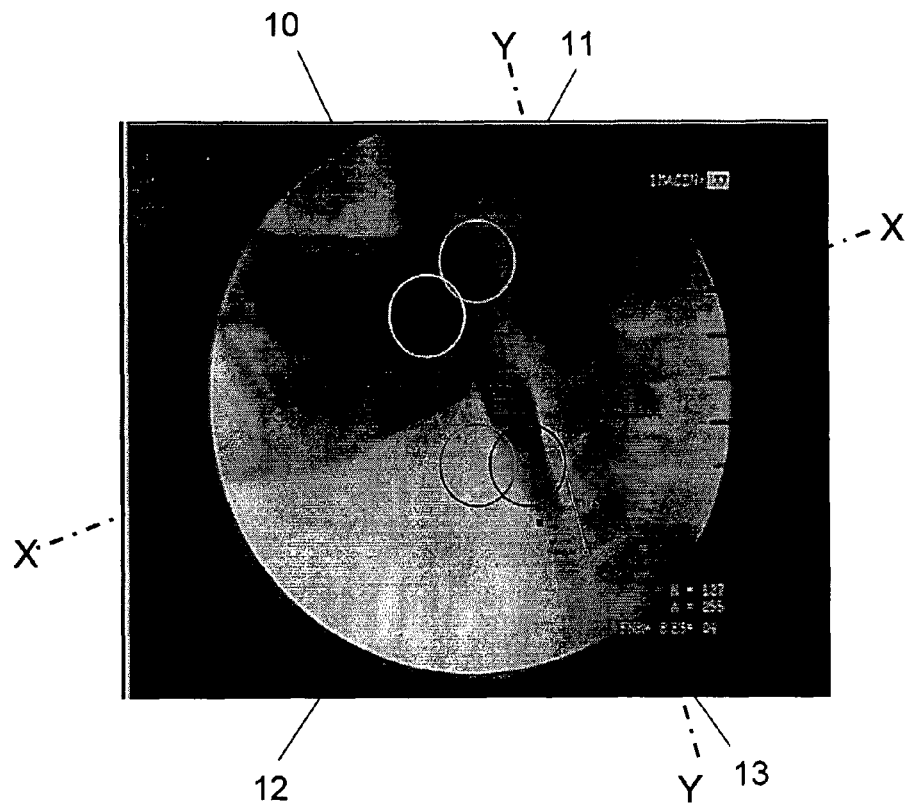
FIG. 3 is an example of display of the displaying and processing of system data.

In said system and procedure for the analysis of the swallowing process in humans, the continuous data sequence is a film of the individual's exposure to x-rays. Said film shows the course of swallowing a substance by the individual or the reflex action of swallowing ones own saliva. An example of an image of the continuous sequence of images or film is that represented in FIG. 3. Said figure shows the x-ray image of the head and neck area of the individual's profile where several anatomical structures (10, 11, 12, 13) of interest in the swallowing process are shown. Specifically, it indicates the structures involved in the closure and opening of the glossopalatine seal 10; the structures involved in the closure and opening of the velopharyngeal seal 11; the structures involved in the closure and opening of the laryngeal vestibule 12; and the structures involved in the closure and opening of the upper oesophageal sphincter 13.

For each one of said sets of anatomical structures (10, 11, 12, 13) involved in said events, the user views the sequence of images or film on the display unit 8 at a rate which is usually slower than the actual rate of the swallowing process, e.g. at half or one tenth of the rate. Generally, each user chooses a rate which they find comfortable, e.g. 25 images per second. With the display at a rate slower than the actual rate, the so-called videofluoroscopic signs (inhalations, penetrations, etc.) can be easily identified and the start and end of the event is easily detectable, e.g. the time when the velopharyngeal seal 11 is opened, as well as the closure thereof. The user processes the continuous data sequence using the display unit 8, marking the start and end of the event and does so by computer peripherals such as a mouse, the keyboard or by printing on a tactile screen.

Figure 4:
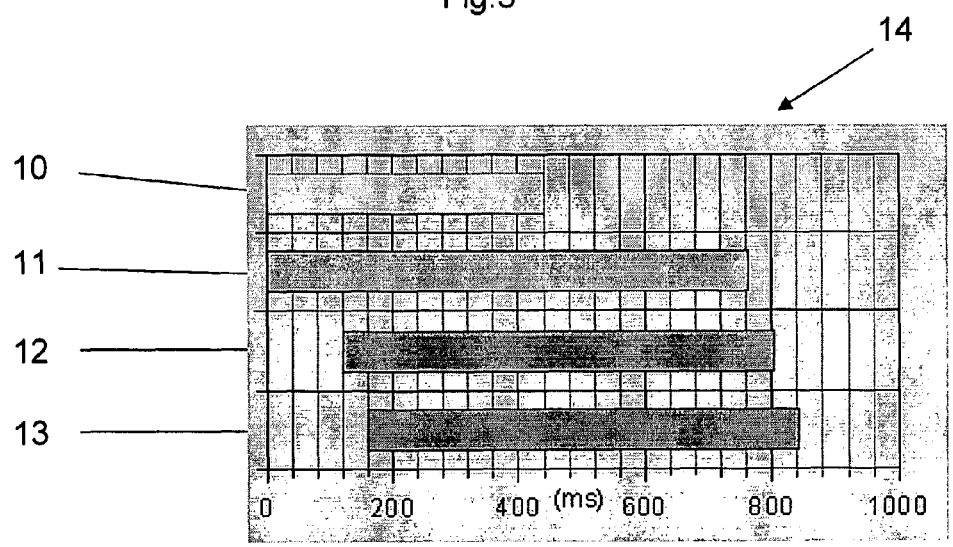
FIG. 4 is an example of graphic representation of quantitative data relating to temporal events of the swallowing process obtained through the system for the analysis of the swallowing process in humans.

The opening and closure sequence, as well as each one of the points of the anatomic structures involved, are parametrized so that graphics 14 such as that represented in FIG. 4 can be represented, wherein, different events of the process are related on a temporal scale. Alternatively, the spatial coordinates with respect to the x-y-z reference axis of each one of the points of the specific anatomical structure can be represented. As a general rule, the x-y spatial reference axis is usually defined as the imaginary line which passes through the individual's vertebral column and a line perpendicular thereto. The system foresees the individual's movements during swallowing and corrects them.

Graphic 14 of FIG. 4 simultaneously represents the time elapsed between the opening and the closure of the glossopalatine seal 10; the time taken by the structures involved in the opening and closure of the velopharyngeal seal 11; the time elapsed for the opening and closure of the structures of the laryngeal vestibule 12; and the time taken by the structures involved in the opening and closure of the upper oesophageal sphincter 13. Said temporal events take the moment of opening of the glossopalatine seal 10 as initial reference instant (T=0). With a graphic 14 such as the one represented, the user can determine if any of the structures or events is delayed or in advance with respect to standardized templates. Said comparison with standardized templates is also performed by the analysis system 1 according to the invention.

Although not represented, other events of interest to perform the analysis of the swallowing process are the instant when the substance to be ingested enters the laryngeal vestibule 12; the instant of inhalation to the respiratory tract; the oral transit time; the pharyngeal transit time, etc. All these events can be equally parametrized and a quantitative and qualitative analysis of the swallowing process can be produced with their analysis and comparison with templates.

Likewise, some of the anatomical structures, whose movement or spatial position is usually represented temporally, correspond to the arrangement of the hyoid bone, the arrangement of arytenoids cartilage, the epiglottis, the location of the front or rear edge of the upper oesophageal sphincter, the digastric fossa of the lower jaw, etc.

Figure 5:
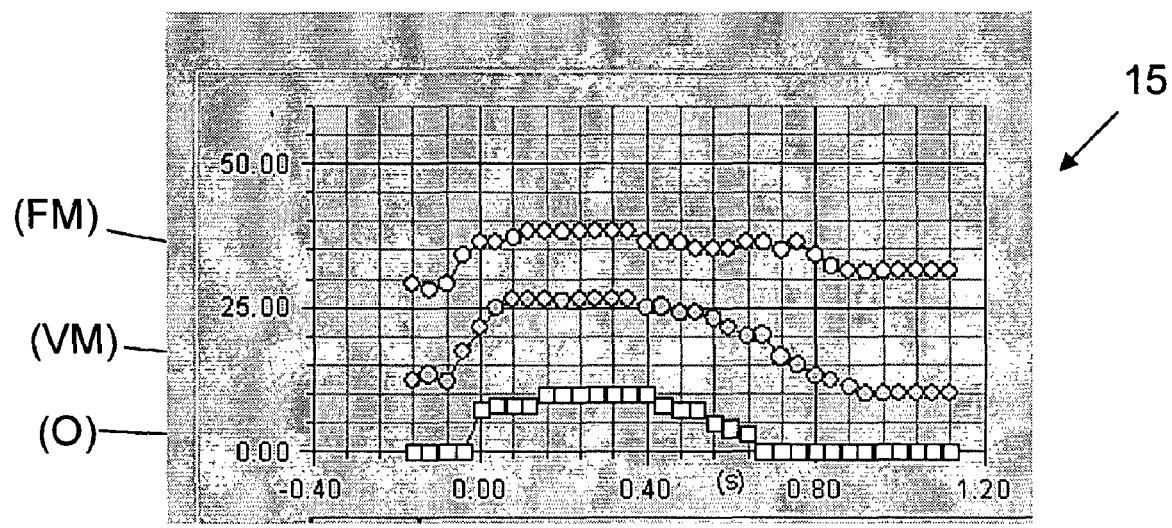
FIG. 5 is an example of graphic representation of quantitative data relating to spatial movements of structures related to the swallowing process obtained through the system for the analysis of the swallowing process in humans.

FIG. 5 consists of a representation of the movement of the hyoid bone during the swallowing process. To produce this graphic 15 using the computer-implemented system 1 according to the invention, the position of said anatomic structure with respect to an x-y-z reference axis is determined. In the case represented, the opening of the upper oesophageal sphincter (O), the forward movement (FM) and the vertical movement (VM) thereof have been quantitatively parametrized. Said points of interest can be shown temporally, meaning the points of each time unit are perfectly defined. With graphics 15 such as that represented in FIG. 5, it is very easy to determine if there are anomalies in the swallowing process derived from a dysfunction in the upper oesophageal sphincter, and, in the same way, it can determine dysfunctions derived from other structures involved in the swallowing process, such as for example, the hyoid bone. Furthermore, the degree or magnitude of the dysfunction can be quantified.

With a computer-implemented system and procedure 1 for the analysis of the swallowing process such as that described, it is possible to parametrize said process and be able to study it qualitatively and quantitatively. The capacity to quantify the swallowing process, also permits producing a study or analysis with greater sensitivity than just the qualitative analysis. It should also be emphasized that the computer-implemented system and procedures according to those disclosed in the invention, are a system and procedure which are quick and easily managed by the user.

A significant advantage of the computer-implemented system 1 and procedure according to the invention is that all the parametrized data are stored in the memory unit (7), meaning that each individual who undergoes analysis of the swallowing process can use their own prior data to perform a comparative study and process evolution, in addition to being able to assign a personalized reference system for each individual.

This system 1 is a great advance as it enables videofluoroscopic sequences to be studied, determining the type and degree of the pathology associated to the anomalous swallowing process; easily identify videofluoroscopic symptoms of the safety and efficiency of swallowing; and simultaneously quantify the temporal and spatial characteristics of the individuals' responses. The invention allows easy viewing of videofluoroscopic sequences, quantitative data and their graphic representation, constituting a diagnostic tool for patients with dysphagia. With a system 1 of this type, the dysfunctions derived from, e.g. the hyoid bone, can be very precisely determined, and the dysfunctions derived from, e.g. an anomaly in the opening or closure of the upper oesophageal sphincter 13, or an anomaly in the opening and closure of the laryngeal vestibule 12, can be very easily distinguished. Furthermore, with said system 1 the diagnosis and monitoring of data of patients with dysphagia can be dealt with quicker and more reliably than the current one, also enabling the objective and quantitative analysis of the swallowing process, thus facilitating the determination of the treatment type by the physical or chemical methods most suitable for the specific dysfunction.

The invention claimed is:

1. A computer-implemented system for analyzing a swallowing process and an oropharyngeal motor response in humans, the computer implemented system comprising:
 an exposure unit for exposing a head and neck area of an individual to external stimuli;
 a data capture unit for capturing data from the individual's response to the external stimuli;
 a data digitization unit for digitizing the captured data;
 a digitized data processing unit for processing the digitized data;
 a memory unit for storing the digitized data and the processed data;
 a processed data display unit for displaying the processed data;
 wherein the digitization unit, the memory unit and the processed data display unit are controlled by a computer program;
 wherein the captured data includes a continuous data sequence;
 wherein the processing unit qualitatively and quantitatively analyzes and measures the captured data with respect to temporal and spatial reference systems, including measuring one or several events or points in the swallowing process time during the data sequence with respect to the initial reference instant (T=0), including the instant of inhalation of a substance to the respiratory tract and at least the moments of opening and closing of the glossopalatine seal, of the velopharyngeal seal, of the laryngeal vestibule and of the upper oesophageal sphincter, said swallowing process and an oropharyngeal motor response being represented by the continuous data sequence; and
 wherein the continuous data sequence display unit includes a display and a processing unit which displays the continuous data sequence at a rate equal to the actual rate of the swallowing process and an oropharyngeal motor response or at a rate which is the result of multiplying the actual rate by a coefficient selectable by the user.

2. The computer-implemented system according to claim 1, wherein the coefficient selectable by the user is less than one.

3. The computer-implemented system according to claim 1, wherein the external stimuli comprises electromagnetic radiation.

4. The system for the analysis of the swallowing process in humans according to claim 3, wherein the electromagnetic radiation comprise x-rays; and
 wherein the continuous data sequence comprises x-ray contrast images.

5. The system for the analysis of the swallowing process in humans according to claim 1, wherein the data capture unit comprises a video camera.

6. A computer-implemented process for analyzing a swallowing process and the oropharyngeal motor response in humans, the computer implemented process comprising:
 a) exposing the area between the head and neck region of the individual to electromagnetic radiation while a substance is swallowed;
 b) capturing data, using a capture unit, in a continuous data sequence;
 c) digitizing the continuous data sequence from the data capture unit;
 d) processing the digitized data and storing the digitized data in a memory unit, so that the sequence of digitized data can then be displayed at an actual rate of the swallowing process or at a rate which is the result of multiplying the actual rate by a coefficient selectable by the user;
 e) determining a spatial axis (x-y-z) and an initial reference instant (T=0) in the data sequence;
 f) displaying or viewing the data sequence at the actual rate of the swallowing process or at the rate which is the result of multiplying the actual rate by the coefficient selectable by the user;
 g) measuring one or several events or points in the swallowing process time during the data sequence with respect to the initial reference instant (T=0), including the instant of inhalation of the substance to the respiratory tract and at least the moments of opening and closing of the glossopalatine seal, of the velopharyngeal seal, of the laryngeal vestibule and of the upper oesophageal sphincter, said swallowing process and an oropharyngeal motor response being represented by the continuous data sequence;
 h) measuring one or several spatial points corresponding to arrangements of anatomic structures involved in the swallowing process during the data sequence with respect to a spatial reference axis (x-y-z), the swallowing process being represented by the continuous data sequence;
 i) comparing intervals of the measured points with standardized templates;
 j) representing the temporal events and the measured spatial arrangements; and
 k) storing the measured events or points from the continuous sequences of data in the memory unit.

7. The process according to claim 6, wherein the data is images and the continuous data sequence is a film.

8. The process according to claim 6, wherein the measurement of one or several spatial points corresponding to movements of anatomical structures involved in the swallowing process comprises the measurement of at least one of the following movements of anatomical structures: the movement of the hyoid bone, the movement of the arytenoids cartilage, or the movement of the front or rear edge of the upper oesophageal sphincter.

9. The process according to claim 6, wherein the electromagnetic radiation comprises x-rays.

10. The process according to claim 7, wherein the measurement of one or several events or spatial points of the swallowing process, the latter represented by the continuous data sequence, comprises the measurement of at least one of the following events:
 the moment of opening and/or closure of the glossopalatine seal;
 the moment of opening and/or closure of the velopharyngeal seal;
 the moment of opening and/or closure of the laryngeal vestibule; and
 the moment of opening and/or closure of the upper oesophageal sphincter.

11. The process according to claim 7, wherein the measurement of one or several spatial points corresponding to movements of anatomical structures involved in the swallowing process comprises the measurement of at least one of the following movements of anatomical structures: the movement of the hyoid bone, the movement of the arytenoids cartilage, and the movement of the front or rear edge of the upper oesophageal sphincter.

12. A method for analyzing a swallowing process and oropharyngeal motor response, and diagnosing dysphagia in a patient, the method comprising:
- exposing the area between the head and neck region of the patient to electromagnetic radiation while a substance is swallowed;
- capturing data, using a capture unit, in a continuous data sequence;
- digitizing the continuous data sequence from the data capture unit;
- processing the digitized data and storing the digitized data in a memory unit of a computer, so that the sequence of digitized data can then be displayed at an actual rate of the swallowing process or at a rate which is the result of multiplying the actual rate by a coefficient selectable by the user;
- determining a spatial axis (x-y-z) and an initial reference instant (T=0) in the data sequence;
- displaying or viewing the data sequence at the actual rate of the swallowing process or at the rate which is the result of multiplying the actual rate by the coefficient selectable by the user;
- measuring one or several events or points in the swallowing process time during the data sequence with respect to the initial reference instant (T=0), including the instant of inhalation of the substance to the respiratory tract and at least the moments of opening and closing of the glossopalatine seal, of the velopharyngeal seal, of the laryngeal vestibule and of the upper oesophageal sphincter, said swallowing process and oropharyngeal motor response being represented by the continuous data sequence;
- measuring one or several spatial points corresponding to arrangements of anatomic structures involved in the swallowing process during the data sequence with respect to a spatial reference axis (x-y-z), the swallowing process and oropharyngeal motor response being represented by the continuous data sequence;
- comparing intervals of the measured points with data for a standardized anatomical event to diagnose dysphagia; representing the temporal events and the measured spatial arrangements; and
- storing the measured events or points from the continuous sequences of data in the memory unit,
- wherein the at least one anatomical event comprises opening and closing of the patient's laryngeal vestibule.

13. The method according to claim 12, wherein the method is implemented by a computer comprising interactive software.

14. The method according to claim 12, further comprising:
- determining a spatial reference axis on the video image;
- measuring a location of at least one anatomical structure, based on the video image, with respect to the spatial reference axis;
- comparing data for the measured location of the at least one anatomical structure with data for a standardized location to diagnose dysphagia;
- wherein the at least one anatomical structure comprises:
  - the patient's hyoid bone;
  - the patient's arytenoids cartilage; or
  - the patient's front or rear edge of the upper oesophageal sphincter.

15. The apparatus according to claim 1, wherein the apparatus is configured to capture, digitize, process, store, and display a swallowing process of at least 840 ms.

16. The apparatus according to claim 1, wherein the apparatus is configured to capture, digitize, process, store, and display a swallowing process of at least 1000 ms.

17. The apparatus according to claim 1, wherein the processing unit measures the moments of opening and closing of the glossopalatine seal.

18. The apparatus according to claim 1, wherein the processing unit measures the moments of opening and closing of the velopharyngeal seal.

19. The apparatus according to claim 1, wherein the processing unit measures the moments of opening and closing of the laryngeal vestibule.

* * * * *